US012343771B2

(12) United States Patent
Van Erp

(10) Patent No.: US 12,343,771 B2
(45) Date of Patent: Jul. 1, 2025

(54) FOOD PROCESSING EQUIPMENT WITH PLASMA ACTIVATED WATER CLEANING

(71) Applicant: GEA FOOD SOLUTIONS BAKEL B.V., Bakel (NL)

(72) Inventor: Joost Van Erp, Nuenen (NL)

(73) Assignee: GEA FOOD SOLUTIONS BAKEL B.V., Bakel (NL)

( * ) Notice: Subject to any disclaimer, the term of this patent is extended or adjusted under 35 U.S.C. 154(b) by 1006 days.

(21) Appl. No.: 16/761,859

(22) PCT Filed: Nov. 6, 2018

(86) PCT No.: PCT/EP2018/080324
§ 371 (c)(1),
(2) Date: Oct. 5, 2020

(87) PCT Pub. No.: WO2019/091972
PCT Pub. Date: May 16, 2019

(65) Prior Publication Data
US 2021/0205856 A1 Jul. 8, 2021

(30) Foreign Application Priority Data
Nov. 7, 2017 (EP) .................................. 17200400

(51) Int. Cl.
*B08B 3/08* (2006.01)
*A22C 17/00* (2006.01)
(Continued)

(52) U.S. Cl.
CPC ............ *B08B 3/08* (2013.01); *A22C 17/0053* (2013.01); *A22C 17/08* (2013.01); *A61L 2/18* (2013.01);
(Continued)

(58) Field of Classification Search
CPC ....... B08B 3/08; B08B 2/041; A22C 17/0053; A22C 17/08; A61L 2/18; A61L 2/22; A61L 2/26; A61L 2202/11; A61L 2202/17
See application file for complete search history.

(56) References Cited

U.S. PATENT DOCUMENTS 2,386,954 A * 10/1945 Kalmar .................... A23B 7/16
426/333
5,863,584 A * 1/1999 Thomas, Jr. .......... A23L 3/3589
99/534
(Continued)

FOREIGN PATENT DOCUMENTS

CA 2651993 A1 * 11/2007 ........... A22B 5/0082
CN 103429090 A 12/2013
(Continued)

OTHER PUBLICATIONS

Machine Translation of CN101069575A (Year: 2007).*
(Continued)

*Primary Examiner* — Sharidan Carrillo
(74) *Attorney, Agent, or Firm* — The Dobrusin Law Firm P.C.

(57) ABSTRACT

A food processing system that includes at least one food and/or feed processing device and at least one cleaning device. The at least one food and/or feed processing device includes at least one part with a surface which during use will come in contact with a food product. The at least one cleaning device is configured for cleaning at least the surface. The at least one cleaning device includes means for providing a cleaning fluid. The cleaning fluid is a plasma activated substance. The at least one cleaning device comprises or is coupled to a device for preparing the plasma activated substance and is provided in a porous structure of the device.

6 Claims, 3 Drawing Sheets

(51) Int. Cl.

| | |
|---|---|
| *A22C 17/08* | (2006.01) |
| *A61L 2/18* | (2006.01) |
| *A61L 2/22* | (2006.01) |
| *A61L 2/26* | (2006.01) |
| *B08B 3/04* | (2006.01) |

(52) U.S. Cl.
CPC .................. *A61L 2/22* (2013.01); *A61L 2/26* (2013.01); *B08B 3/041* (2013.01); *A61L 2202/11* (2013.01); *A61L 2202/17* (2013.01)

(56) References Cited

U.S. PATENT DOCUMENTS

| | | | |
|---|---|---|---|
| 9,550,007 B2* | 1/2017 | Tsai | .................. A61L 2/186 |
| 2013/0104742 A1 | 5/2013 | Deo et al. | |
| 2013/0337128 A1 | 12/2013 | Van Gerwen et al. | |
| 2014/0100277 A1 | 4/2014 | Gray et al. | |
| 2015/0283283 A1* | 10/2015 | Schieven | .................. A61L 9/22 |
| | | | 422/123 |
| 2016/0015038 A1* | 1/2016 | Ferrell | .................. A23B 7/154 |
| | | | 800/298 |
| 2017/0050332 A1 | 2/2017 | Bauer et al. | |
| 2017/0156392 A1* | 6/2017 | Brennan | .................. B08B 3/042 |
| 2019/0105418 A1* | 4/2019 | Jaques | .................. B08B 3/02 |

FOREIGN PATENT DOCUMENTS

| | | | | |
|---|---|---|---|---|
| CN | 103501620 | A | 1/2014 | |
| CN | 104150558 | A | 11/2014 | |
| CN | 104707154 | A | 6/2015 | |
| CN | 105166030 | A | 12/2015 | |
| CN | 106178028 | A | 12/2016 | |
| CN | 106455591 | A | 2/2017 | |
| CN | 205999054 | U | 3/2017 | |
| CN | 206173024 | U | 5/2017 | |
| EP | 3146983 | A1 * | 3/2017 | .............. A61L 2/14 |
| WO | WO-02058449 | A2 * | 8/2002 | .............. A61L 2/08 |
| WO | 2012/084215 | A1 | 6/2012 | |
| WO | WO-2014055812 | A1 * | 4/2014 | ............ A01N 37/02 |
| WO | 2015/169812 | A1 | 12/2015 | |
| WO | 2016/096751 | A1 | 6/2016 | |
| WO | WO-2016146519 | A2 * | 9/2016 | .............. A22C 7/00 |
| WO | 2016/197224 | A1 | 12/2016 | |

OTHER PUBLICATIONS

Yasin Sem et al: "Sterilization of Food Contacting Surfaces via Non-Thenal Plasma Treatment: A Model Study with *Escherichia coli*—Contaminated Stainless Steel and Polyethylene Surfaces", Food and Bioprocess Technology; An International Journal, vol. 6, No. 12, dated Dec. 8, 2012.
Leipold et al. Decontamination of a Rotating Cutting Tool During Operation by means of Atmospheric Pressure Plasmas 2010.
International Search Report and Written Opinion for International Application PCT/EP2018/080324, dated Feb. 11, 2019.
International Preliminary Report on Patentability for International Application PCT/EP2018/080324, dated Feb. 24, 2020.
Japanese Office Action dated Nov. 18, 2022, for Japanese Application 2020-524439.

* cited by examiner

FOOD PROCESSING EQUIPMENT WITH PLASMA ACTIVATED WATER CLEANING

FIELD OF THE INVENTION

The present invention relates to a food and/or feed processing device, a food processing system and to a method for cleaning, sanitizing, disinfecting and/or sterilizing a food contacting surface of a food and/or feed processing device.

DESCRIPTION OF RELATED ART

Such food and/or feed processing devices include among others former, in which a mass of a food product, is filled into cavities of a drum or a plate. The thus formed patty will then be discharged at another location of the former. In order to help expelling the patty from the cavity, it is known to employ mechanical pusher means or air and/or liquid which is introduced, in the case of a rotating drum, from the inner side of the drum. Because such drums comprise holes or gaps, the surface as well as the underlying structure of the drum, which includes the cavities, is considered to be at least partially porous. Such a mould drum is e.g. disclosed in patent application WO 2015/169812 A1, which is fully incorporated herein with regard to the specific design of the former and in particular the drum.

In such devices, as in all food and/or feed processing devices, the food product(s) will touch surfaces and may leave a biofilm. Due to hygiene standards and in order to avoid any contamination, at least all surfaces which are in contact with the food product must be thoroughly cleaned regularly. Therefore, cleaning apparatuses have been provided. The parts of the food and/or feed processing device which have to be cleaned, such as the drum of a former, may be taken out of the device and transferred to a cleaning apparatus. In particular concerning the drum of a former, such a cleaning apparatus is e.g. disclosed in patent application WO 2012/084215 A1, which is fully incorporated herein with regard to the cleaning apparatus.

In the cleaning apparatus or device, cleaning takes place in accordance with a lengthy cleaning protocol. This may include multiple steps of applying a cleaning fluid, e.g. water in combination with a cleaning product, rinsing, applying a disinfectant and/or drying.

In other food and/or feed processing devices, e.g. brine handling devices, needles inject a fluid, such as brine, into a food product, e.g. meat. Any excess fluid will be recycled. For this purpose, the fluid will pass several filters and/or membranes. All of the fluid carrying tubes as well as the filters and/or membranes need to be cleaned as well. Due to the installation, removal and remote cleaning such a process is often cumbersome. Therefore, so called clean-in-place procedures have been developed with which it is possible to clean parts within the device without having to remove the parts first.

Yet, all the above described methods are time-consuming, require several different cleaning fluids and/or steps and are difficult to integrate into known production lines while fulfilling the high hygienic standards required when working with food products.

There is therefore a constant need to improve the known cleaning procedures in food processing systems. A further objective of the present invention is to facilitate cleaning within systems which employ fluids.

The problem is solved by a food processing system, comprising at least one food and/or feed processing device and at least one cleaning device, wherein the food and/or feed processing device comprises at least one part with a surface which during use will come in contact with a food product, wherein the cleaning device is configured for cleaning at least the at least one surface, wherein the cleaning device comprises means for providing a cleaning fluid, wherein the cleaning fluid is plasma activated substance, for example a fluid like water and/or a gas.

Brief Summary of the Invention

The present invention relates to a food and/or feed processing system. Such systems may comprise one or more distinct devices, wherein distinct is to be understood as separate, i.e. the devices are substantially independent from each other. Preferably, each device comprises its own casing and/or is moveable independently from other devices. Nevertheless, the devices may be connected to each other, such as via pipings, tubes, electrical, pneumatic and/or hydraulic connections. The devices may as well form an assembly line. E.g. a former for forming patties from a mass of food product and a subsequently arranged packaging machine may an assembly line but may nevertheless be distinct devices. Alternatively, at least one or more devices are integrated into one device, frame and/or casing. A food and/or feed processing device according to the invention is any device that produces, modifies, handles, processes and/or packages food. In particular, although not restricted to, this invention refers to meat processing machines. With meat processing machines, hygiene is particularly important and contamination by means of residuals and/or biofilms is high. All of the considerations regarding food processing systems in this application apply as well to feed processing systems. Such systems and/or devices are used to produce feed for animals. In general, the same considerations as for food processing systems and/or devices apply for feed processing systems and/or devices as well.

The system according to the present invention further comprises a cleaning device. Such a cleaning device may be separate from the food and/or feed processing device or may be integrated within the food and/or feed processing device or another device. The cleaning device preferably comprises means such as supply lines for supplying at least one cleaning medium, preferably a fluid. The cleaning device preferably further comprises a reservoir for storing and/or producing a cleaning fluid and more preferably comprises a sink for collecting used cleaning fluids and/or residual fluids. Even more preferably, the cleaning device comprises a recycling system for at least partially recycling the cleaning fluid. Such a recycling system may comprise filters, membranes and/or recuperators or heat exchangers. Preferably, the cleaning device comprises a bath for bathing the food and/or feed processing device part in the cleaning fluid. Alternatively or additionally, the cleaning device comprises nozzles for spraying the cleaning fluid and/or outlets for showering or dousing the part.

Now, according to the present invention, the cleaning fluid is plasma activated substance, preferably a gas and/or water. Plasma activated water is water that has been treated by contact with a plasma. The water may be tap water or purified water, including distilled water, double-distilled water and/or deionized water. After treatment, the water will contain nitrogen oxide and hydrogen peroxide. Additionally, the water will be more acidic. Thus, plasma activated water (in the following abbreviated by PAW) has excellent antibacterial and anti-biofilm properties. Furthermore, PAW has a very low pH-value. Therefore, PAW may substitute water and/or a separate cleaning agent. Nevertheless, for redundancy purposes, the cleaning device according to the invention may preferably use additional cleaning agents. Concerning the properties and the production of PAW, it is herewith referred to the application WO 2016/096751 A1, whose disclosure is herewith fully incorporated, in particular with regard to the production and properties of PAW and/or with regard to atmospheric pressure plasma For the purpose of this invention, cleaning is preferably meant to comprise sanitizing, disinfecting and/or sterilizing. Hence, in particular a clean-in-place method may comprise a sanitize-in-place method.

According to a preferred embodiment of the present invention, the surface as well as the underlying structure of the food and/or feed processing device is at least partially porous. In particular, the surface is at least partially a porous surface. This shall include a surface made of a porous material and/or a surface being manipulated or processed to be porous. Preferably, the surface comprises cavities, holes and/or orifices. Preferably, the surface is part of a removable or non-removable part of the food and/or feed processing device. More preferably, the part is a moulding drum, a moulding plate, a mixing drum and/or an injector. Preferably, the part comprises flow distribution means, such as channels, for guiding a fluid flow during use. More preferably, the part comprises cleaning fluid distribution means, wherein even more preferably, the cleaning fluid distribution means are connected to or reversibly connectable to the flow distribution means for distributing the cleaning fluid during cleaning.

With a Atmospheric-pressure plasma device it is also preferred to activate water laying down on the surface or water in a porous structure.

According to a preferred embodiment of the present invention, the food and/or feed processing device is a freezer, a former, a coater, a fryer, a cooker, a mixer, a tumbler, a grinder, a bowl chopper, a food injector or a brine preparing and/or injecting device.

In particular, in a food injector, the food product, e.g. meat, will be injected by needles and brine will be forced out of holes in the needles. In case not all brine ends up in the food product and/or remains in the food product after the injection, the excess brine is afterwards collected and recycled. Before re-entering the needles, the excess brine needs to be filtered. A filter system of a food injector system preferably comprises multiple filters. By applying PAW within the cleaning procedure for the filters and/or needles of the injector, the good anti-biofilm activity, antibacterial activity and disinfecting effect is advantageously used and furthermore, using PAW results in a reduced cleaning procedure time. PAW is preferably also applicable in systems to prepare brine, for instance in cleaning the brine pipelines.

According to a preferred embodiment of the present invention, the cleaning device comprises or is coupled to a device for preparing the plasma activated water. More preferably, the cleaning device is configured to produce or prepare PAW and/or a a plasma activated gas in-line. It is herewith advantageously possible to produce the PAW in place according to the current requirement without having to store volumes of PAW. In particular, the cleaning device advantageously only requires a tap water connection and electric current for inducing a plasma and/or a gas.

According to a preferred embodiment of the present invention, the food and/or feed processing device comprises or is coupled to the cleaning device such that the food and/or feed processing device is configured for a clean-in-place and/or sanitize-in-place method. As mentioned before, PAW and/or an atmospheric-pressure plasma holds antibacterial properties. Depending on the concentration and/or dilution with normal, e.g. tap water, PAW may be used for cleaning, sanitizing or disinfecting. A clean-in-place method designates a method for cleaning within the food production device, i.e. no parts need to be removed for remote cleaning. The clean-in-place method follows a predetermined protocol to ensure compliance with hygiene regulations after cleaning. By using PAW and/or an atmospheric-pressure plasma, the procedure may advantageously shortened, i.e. e.g. less steps and/or shorter times, without jeopardizing the result and/or using chemicals According to a preferred embodiment of the present invention, the part comprises means, in particular at least one opening or channel, for transmitting a fluid such as air and/or atmospheric-pressure plasma or water, wherein preferably the part is connected to or reversibly connectable to the means for supplying the plasma activated water to the means for transmitting a fluid. Preferably, the part comprises cleaning fluid transmitting means, such as openings or channels, which are dedicated for the PAW. Alternatively or additionally, the part comprises fluid transmitting means which, in particular during use, are configured for transmitting at least one fluid other than PAW. Hence, it is advantageously possible to ensure cleaning by providing dedicated fluid transmitting means and/or to facilitate the structure of the part by using already existing fluid transmitting means.

According to a preferred embodiment of the present invention, the food and/or feed processing device and/or the cleaning device comprise an air supply for supplying, in particular pressurized, air. Preferably, the air is provided during use for expelling. Additionally or alternatively, the air is provided during cleaning for drying.

Another subject matter of the present invention is a food and/or feed processing device comprising at least one fluid transmitting means, such as a channel or tube, for supplying a fluid, such as air or water, wherein the device is configured such that at least during a predetermined period of time, plasma activated water is supplied through the fluid transmitting means, wherein the food and/or feed processing device is preferably reversibly connectable to or connected to a supply for supplying the plasma activated water. Preferably the food and/or feed processing device is part of the food processing system according to the present invention. The inventive device advantageously is easily cleanable by means of the PAW.

The disclosure made regarding this particular subject matter of the invention also applies to the other subject matters of the present invention. Features from the device can be incorporated into the system and vice versa.

According to a preferred embodiment of the present invention, PAW instead of water is used in food processing devices provided with fluid transmitting means, such as water pipelines. In case cold water within a pipeline will be subjected to higher environmental temperatures, legionella contamination may occur, in particular in the temperature range from 25° C. to 37° C., whereas above 55° C., the bacteria will die. In stationary water, for instance at drain points, water filling points and/or water stops, legionella bacteria can grow to large numbers. Biofilm contaminated water pipes are also a source for legionella bacteria. By rinsing with hot water, the bacteria will die—the biofilm will however remain. In all above-mentioned situations, the use of PAW is advantageous to prevent bacteria growth and/or biofilm creation.

Another subject matter of the present invention is a method for cleaning, sanitizing, disinfecting and/or sterilizing a food contacting surface of a food and/or feed processing device, in particular according to the present invention and/or preferably of a food processing system according to the present invention, wherein after use of the food and/or feed processing device, preferably after every use, a cleaning step is carried out, wherein during the cleaning step, the surface is treated with plasma activated water.

The disclosure made regarding this particular subject matter of the invention also applies to the other subject matters of the present invention. Features from the method can be incorporated into the system and/or the device and vice versa.

According to a preferred embodiment of the present invention, the cleaning step comprises rinsing, bathing, showering, submerging and/or spraying the surface with the plasma activated water. The person skilled in the art understands that this may depend strongly on the specific requirements in each case. Advantageously, bathing ensures a proper soaking whereas spraying or rinsing may be preferable in order to detach food residuals which adhere to the surface. Preferably, during any of the above steps, the part and/or surface and the PAW are moved relative to each other. In a bath, the part may be moved and alternatively or additionally, a moving nozzle may spray the PAW on the surface.

According to a preferred embodiment of the present invention, wherein the cleaning step is carried out in the food and/or feed processing device, wherein the method is a clean-in-place (CIP) and/or sanitize-in-place (SIP) method. Preferably, the CIP/SIP method comprises at least one, more preferably multiple steps. Even more preferably, more than one step, e.g. two, three, four or five steps, include bringing the surface to be cleaned in contact with PAW. Preferably, at least two steps differ at least in the kind of contact, e.g. rinsing, spraying, showering, etc. Preferably, the CIP/SIP method comprises at least one drying step. More preferably, the CIP/SIP method comprises at least one pre-treatment step, wherein in particular during the pre-treatment step, the surface is mechanically cleaned and/or rinsed with a fluid other than PAW, such as tap water, purified water or air, to remove larger residuals.

According to a preferred embodiment of the present invention, before the cleaning step, the part comprising the surface to be cleaned is removed from the food and/or feed processing device and preferably transferred to the cleaning device for cleaning. Preferably, the removal and/or transfer is carried out by means of a transfer device. Such transfer devices are known and help carrying the often heavy-weighted parts of food processing machines. Preferably, the food and/or feed processing device is cleaned separately from the part. For example, it may be necessary to remove the part in order to access potentially contaminated areas of the food processing machine. Alternatively, the part comprises a complex geometry and therefore, in order to clean it properly in compliance with hygiene regulations, it needs to be removed from the food and/or feed processing device.

According to a preferred embodiment of the present invention, during the cleaning step, the part and/or the surface is moved, preferably rotated. Thus, advantageously, a better contact with the PAW and hence an improved cleaning effect is achieved.

According to a preferred embodiment of the present invention, after the cleaning step, a drying step is carried out, preferably by directing a stream of pressurized air at the surface or through the porous structure.

According to a preferred embodiment of the present invention, during the cleaning and/or the drying step, a premixed flow is applied to the surface, wherein the premixed flow comprises a gas, in particular air, and a liquid, in particular plasma activated water. Thus, advantageously, due to the lower viscosity of such a premixed flow, a better distribution of the PAW is ensured while maintaining the good cleaning properties of PAW.

BRIEF DESCRIPTION OF THE DRAWINGS

The inventions are now explained according to the figures. These explanations do not limit the scope of protection and apply to all embodiments of the present invention likewise.

DETAILED DESCRIPTION OF THE INVENTION

Figure 1:
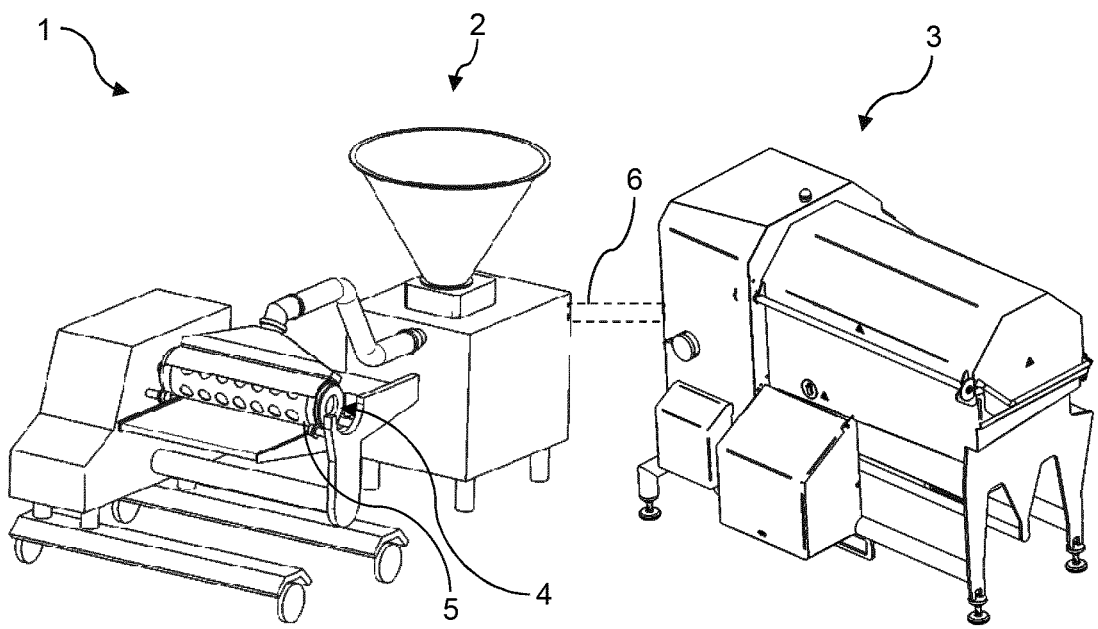
FIG. 1 shows a food processing system according to a preferred embodiment of the present invention.

In FIG. 1, a food processing system 1 according to a preferred embodiment of the present invention is shown. While the present invention relates generally to food and/or feed processing devices 2 and in particular to meat processing machines, the aspects of the invention will be explained by referring exemplarily to a former. Such a former is designed to form food patties from a mass of a food product. For example, hamburgers or chicken nuggets may be produced by such a former.

The former comprises a hopper in which the food product mass, e.g. minced meat, is entered. The mass is then forwarded through a pipe towards a rotating moulding drum 4. Such a moulding drum 4 comprises substantially a cylindrical form and is rotated around its longitudinal axis A. It comprises a plurality of cavities 7, which may be arranged in rows. The food product mass is pressed into the cavities 7. When the drum 4 has rotated to a transfer position, here arranged below the drum 4 and comprising an endless transfer belt, the formed food product, e.g. the patty, is expelled from the cavity. As due to the adhesiveness of most formed food products gravity alone may not be sufficient to reliably expel all food products. Therefore, the drum 4 comprises an at least partially porous surface 5 and the underlying structure is designed to be partially porous as well, meaning that the surface and/or the underlying structure comprise openings in the cavities 7 through which selectively a stream of fluid, e.g. pressurized air, may be forced. For this purpose, the openings are part of flow distribution means 8, which comprise channels, which likewise are preferably arranged in rows. The channels are connected to a fluid supply, here a pressurized air supply.

After prolonged use, food product residuals may remain in the cavities 7 or on the surface 5 of the drum. Additionally, a biofilm may have built up on the surface 5. For hygienic reasons and in order to avoid any (cross) contamination, the drum 4 needs to be cleaned regularly. This may be effectuated in a cleaning device 3. The food and/or feed processing device 2, here the former, may be configured according to clean-in-place procedures/methods, such as indicated by the dashed lines which symbolize cleaning fluid distribution means 6.

For instance, the cleaning device 3 may provide a cleaning fluid which is then transferred via the cleaning fluid distribution means 6 to the food and/or feed processing device 2, where, according to a predetermined protocol, the relevant parts 4 and surfaces 5, which came in contact with the food product, are cleaned. The position of the cleaning fluid distribution means 6 is purely here purely symbolic. The person skilled in the art understands that in order to clean the drum 4, the cleaning fluid distribution means 6 may have to be arranged differently. Additionally, usually further distribution means will be provided to collect and discharge the used cleaning fluid. It is e.g. transferred back to the cleaning device 3 where it will be filtered, cleaned and recycled.

Alternatively, the drum 4, and/or other parts 4 of the food and/or feed processing device 2, may be removed from the processing device and transferred to the cleaning device 3. In such a case, cleaning fluid distribution means 6 are not necessary. Instead, the drum 4 will be introduced into the cleaning device 3 and cleaned.

As mentioned before, the present invention applies to other food and/or feed processing devices such as freezers, tumblers, mixers, grinders, bowl choppers, food injectors, brine preparing and/or injecting devices, coaters, fryers, cookers or other devices which require regular cleaning with regard to hygiene regulations as well. Even with formers, such as explained above, the invention shall not be restricted to rotating drum formers. Another possible application are formers using moulding plates.

According to the present invention, the cleaning fluid is at least partially plasma activated water (PAW). PAW is produced by contacting water—tap water or any kind of purified water such as distilled, double-distilled or deionized water—with a plasma. A plasma is a state of matter similar to an ionized gas. It may be produced by subjecting a (dielectric) gas or fluid to high currents. Hence, a plasma producing device requires substantially a fluid and electricity as resources.

By contacting water with the plasma, the water will obtain nitrogen oxide and hydrogen peroxide and become more acidic, corresponding to a lower pH value. Details on plasma activated water are disclosed in the patent application WO 2016/096751 A1, whose content is fully incorporated herewith, in particular with regard to PAW and devices for producing PAW. The thus produced PAW comprises antibacterial and anti-biofilm properties and can thus be used as a detergent, a disinfectant and/or sanitizer, which is generally comprised as a cleaning fluid in the following.

Preferably, the cleaning device 3 comprises a device for producing PAW and/or a reservoir for storing PAW and/or has a Atmospheric-pressure plasma device to produce PAW on the surface.

Usually, cleaning of food producing devices' 2 parts 4 comprise multiple and/or repeated steps or pre-cleaning, applying a cleaning fluid, rinsing and drying. By using PAW as a cleaning fluid, many of those steps may be omitted, as PAW may be used for cleaning as well as for rinsing. Due to the good cleaning properties, repeated steps may be unnecessary and as water is basically non-toxic with regard to food products, extensive rinsing steps in order to reliably remove all traces of a detergent are unnecessary as well.

Thus, whether a CIP method is used or the drum 4 is transferred to the cleaning device 3, the cleaning process will be more effective. Additionally, in a very advantageous manner, no additional and/or limited cleaning fluids are required. Storing and applying detergents comprising serious health hazards is thereby advantageously avoided.

Figure 2:
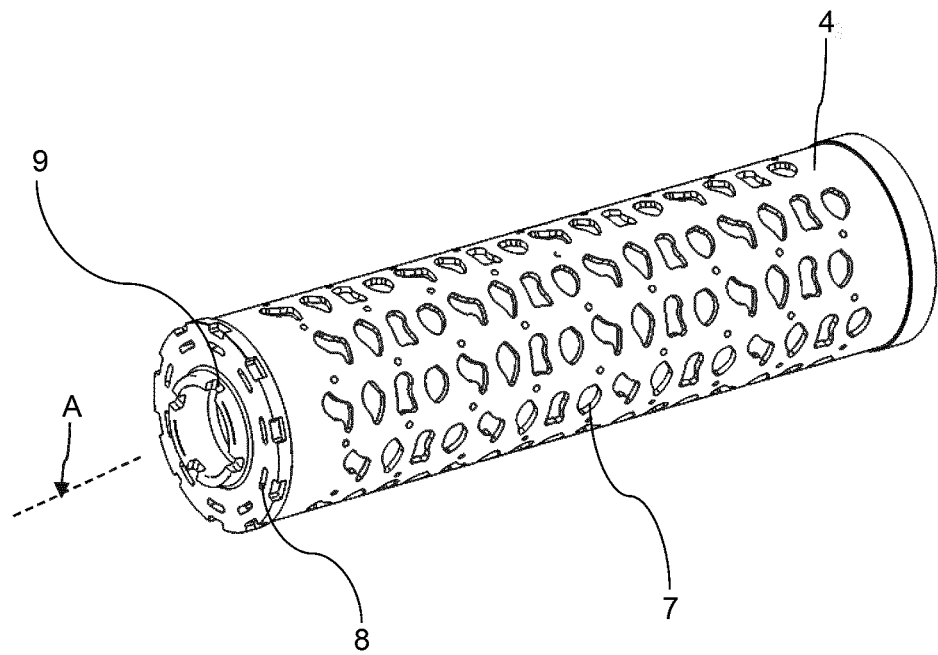
FIG. 2 shows a part of a food and/or feed processing device comprising a surface to be cleaned according to a preferred embodiment of the present invention.

In FIG. 2, a part 4 of a food and/or feed processing device 2 comprising a surface 5 to be cleaned according to a preferred embodiment of the present invention is shown. As explained with regard to FIG. 1, here the part 4 is a rotating moulding drum 4 of a former. The drum 4 comprises a cylindrical form with a longitudinal axis A around which it is rotatable. The drum 4 comprises multiple rows of, e.g. differently formed, cavities 7. In order to securely push out the formed food product, the drum 4 comprises flow distribution means 8, in this case channels for distributing pressurized air. Each cavity preferably comprises a, in particular independently controllable, nozzle. The former comprises an air supply which is connectable to the flow distribution means 8 of the drum 4. At the right position, the pressurized air is expelled through the nozzles of a row and the food products are pushed out of the cavities 7.

In order to ensure good cleaning, in particular when the former is adapted for CIP, the drum 4 further comprises cleaning fluid distribution means 9. In this case, these cleaning fluid distribution means 9 comprise circumferentially distributed openings through which the PAW may enter into the flow distribution means 8 for cleaning the drum 4 from the inside as well. Thus, potentially channel blocking food residuals may be removed. Any other form of cleaning fluid distribution means 9 may be suitable as well, e.g. a dedicated connection for PAW may be provided in the drum 4 and/or the former.

Alternatively or additionally, a premixed fluid flow is applied at one point during the cleaning process, wherein the premixed fluid flow comprises PAW. For example, PAW may be introduced into an air stream in order to ensure a better flow distribution and/or in order to provide a drying air stream with antibacterial and anti-biofilm properties.

Figure 3:
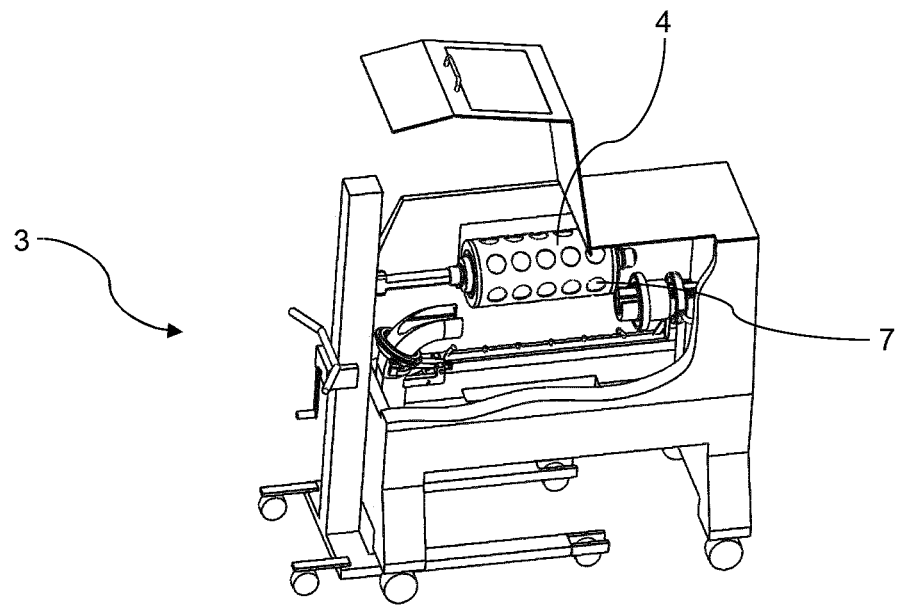
FIG. 3 shows a cleaning device with a part removed from a food and/or feed processing device according to a preferred embodiment of the present invention.

In FIG. 3, a cleaning device 3 with a part 4 removed from a food and/or feed processing device 2 according to a preferred embodiment of the present invention is shown. In this case, the drum 4 is removed from the former and transferred via a transfer device, which is visible on the left of the drawing into the cleaning device 3. The transfer device may be omitted, but is helpful for securely transferring the usually heavy drum 4. As shown in FIG. 3, the drum 4 is fixed in a bearing and enclosed by a casing, in order to prevent any substance from exiting the cleaning device 3. The cleaning inside the cleaning device 3 may comprise bathing, showering, spraying, rinsing and/or drying steps. According to the present invention, in at least some of the above-mentioned steps, preferably in all steps, PAW is used alone or in combination with other substances. Preferably, at the bottom of the cleaning device, a sink is provided for collection the used cleaning fluid. More preferably, the used cleaning fluid is recycled by filtering it.

Even though not shown in FIG. 3, the cleaning device 3 may be connected to or comprise a PAW production device. Thus, the PAW required for cleaning is produced in-line.

Figure 4:
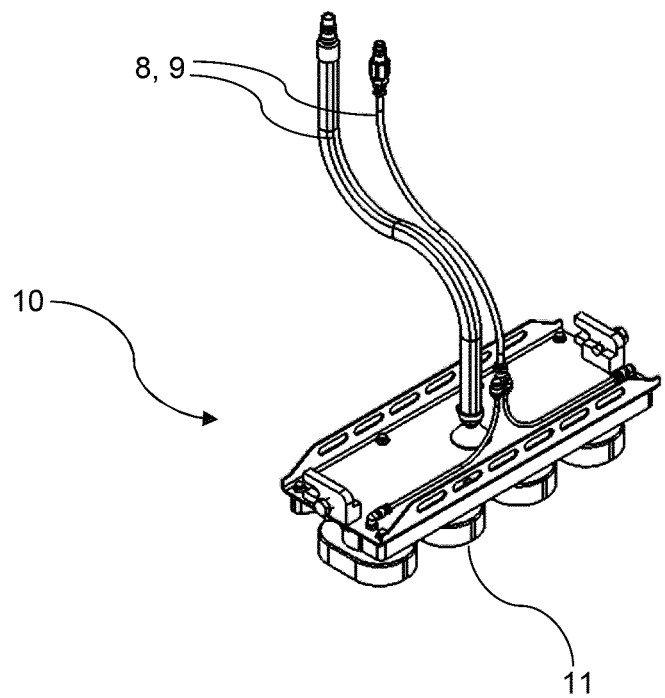
FIG. 4 shows a part of a food and/or feed processing device comprising a surface to be cleaned according to a preferred embodiment of the present invention.

In FIG. 4, a part 4 of a food and/or feed processing device 2 comprising a surface 5 to be cleaned according to a preferred embodiment of the present invention is shown. In the case moulding plates are used in lieu of a moulding drum, knock-out units 10 as shown in FIG. 4 may be used for pushing the food products out of the cavities. Here, the knock-out unit 10 comprises a row of four knock-out cups 11 as well as flow and/or cleaning fluid distribution means 8, 9. In particular, the knock-out unit 10 may comprise dedicated flow distribution means 8 and cleaning fluid distribution means 9 or the flow distribution means 8 may be used for cleaning as cleaning fluid distribution means 9.

Alternatively or additionally, one of the shown connection tubes serves as a pneumatic, hydraulical and/or electrical connection line.

Figure 5:
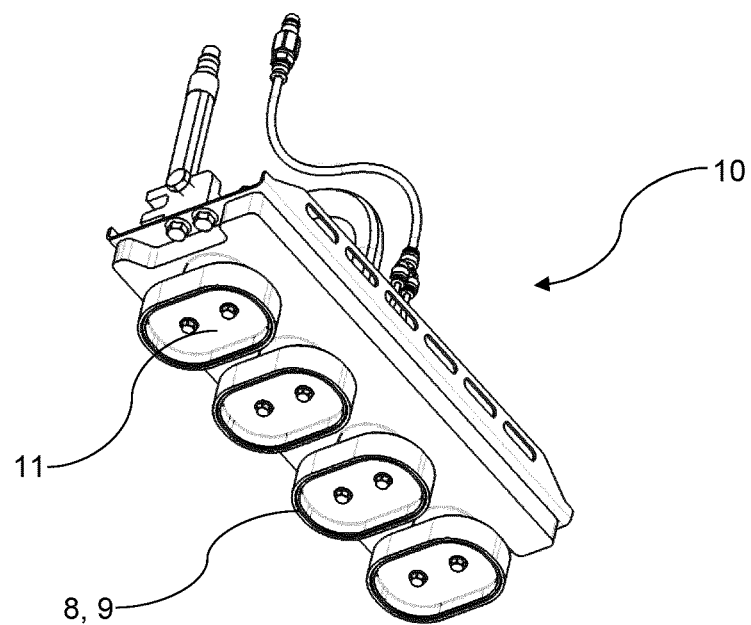
FIG. 5 shows the part of a food and/or feed processing device of FIG. 4 according to a preferred embodiment of the present invention.

In FIG. 5, the part 4 of a food and/or feed processing device 2 of FIG. 4 according to a preferred embodiment of the present invention is shown from a different perspective. In FIG. 5, a gap surrounding the knock-out cups 11 is identifiable. In use, air may be expelled through this gap to help pushing out the food products. Thus, the gap is part of the flow distribution means 8. Preferably, in cleaning, a premixed PAW and air flow will be forced through the gaps to remove blocking objects and for removing biofilms and cleaning the knock-out unit 10. For this purpose, the gap functions, depending on the situation, as cleaning fluid distribution means 9.

LIST OF REFERENCE SIGNS 1 food processing system
2 food and/or feed processing device
3 cleaning device
4 part
5 (porous) surface
6 fluid transmitting means
7 cavities
8 flow distribution means
9 cleaning fluid distribution means
10 knock-out unit
11 knock-out cups
A axis

The invention claimed is:

1. A method for cleaning, sanitizing, disinfecting and/or sterilizing a food contacting surface of a cylindrical moulding drum with a cleaning device, the cylindrical moulding drum is configured to rotate about its longitudinal axis and comprises one or more cavities into which a food product mass is pressed into to form a food product, the one or more cavities comprising an at least partially porous surface,
wherein the method comprises the steps of:
  treating the food contacting surface of the cylindrical moulding drum after the food product is formed in the one or more cavities with the plasma activated water;
  wherein the method comprises supplying tap water and electric current to the cleaning device;
  wherein the cleaning device comprises either, i) an atmospheric-pressure plasma device to produce the plasma activated water, or ii) a device coupled to the cleaning device to produce the plasma activated water;
  wherein before the treating step, the method comprises a pre-treatment step, where the food contacting surface of the cylindrical moulding drum is cleaned and/or rinsed with a fluid other than the plasma activated water;
  wherein after the treating step, the method comprises a drying step that includes applying a mixture having a lower viscosity than the plasma activated water to the food contacting surface of the cylindrical moulding drum, wherein the mixture comprises air and/or the plasma activated water.

2. The method according to claim 1, wherein the method comprises rinsing, bathing, showering, submerging, and/or spraying the food contacting surface with the plasma activated water.

3. The method according to claim 1, wherein the method is a clean-in-place and/or sanitize-in-place method.

4. The method according to claim 1, wherein the cylindrical moulding drum is transferred to the cleaning device for cleaning.

5. The method according to claim 1, wherein the food contacting surface is moved or rotated during the cleaning.

6. The method according to claim 1, wherein the method comprises a step of collecting the plasma activated water and then filtering, and/or recycling the plasma activated water.

* * * * *